United States Patent [19]
Smith et al.

[11] Patent Number: 5,733,785
[45] Date of Patent: Mar. 31, 1998

[54] AUTOMATED URINALYSIS METHOD FOR DETECTING BLOOD IN URINE

[75] Inventors: Jack V. Smith, St. Petersburg; Jesse M. Carter, Tampa, both of Fla.

[73] Assignee: Chinera Research Chemical, Inc., Largo, Fla.

[21] Appl. No.: 787,623

[22] Filed: Jan. 23, 1997

Related U.S. Application Data

[63] Continuation of Ser. No. 582,093, Jan. 2, 1996, abandoned, which is a continuation-in-part of Ser. No. 407,642, Mar. 21, 1995, abandoned, which is a continuation-in-part of Ser. No. 68,956, May 28, 1993, abandoned.

[51] Int. Cl.$^6$ .................. G01N 21/78; G01N 33/493
[52] U.S. Cl. .................. 436/66; 436/164; 436/171; 436/904
[58] Field of Search .............. 436/66, 135, 904, 436/164, 171–172; 422/56–58, 61

[56] References Cited

U.S. PATENT DOCUMENTS

| | | | |
|---|---|---|---|
| 3,907,503 | 9/1975 | Betts et al. | 422/67 |
| 4,755,472 | 7/1988 | Ismail et al. | 436/66 |
| 5,042,502 | 8/1991 | Guirguis | 422/60 |
| 5,089,420 | 2/1992 | Albarella et al. | 436/66 |

*Primary Examiner*—Lyle A. Alexander
*Attorney, Agent, or Firm*—Larson Larson, P.A.; Herbert W. Larson

[57] ABSTRACT

Detecting red blood cells in a patient's urine by placing an aliquot of the urine in an automated analyzer sampling cup. The urine is transferred to a cuvette mounted within the automated analyzer and one or more reagent compositions in an aqueous medium is injected into the cuvette. The reagent contains a buffer to adjust pH, chemicals to remove substances in the urine that interfere with colorimetric photometry, a compound to lyse the red blood cells in the urine, a substrate to react with the hemoglobin, a color indicator and a surfactant to improve fluid mechanics. The sample is read against a standard using a pre-programmed monochromatically specified wavelength to determine the presence or absence of blood cells in the patient's urine.

6 Claims, No Drawings

AUTOMATED URINALYSIS METHOD FOR DETECTING BLOOD IN URINE

PRIOR APPLICATION

This application is a file wrapper continuation of application Ser. No. 08/582,093, filed Jan. 2, 1996, now abandoned, which is a continuation-in-part of application Ser. No. 08/407,642, filed Mar. 21, 1995, now abandoned which is a continuation-in-part of application Ser. No. 08/068,956, filed May 28, 1993 (now abandoned).

BACKGROUND OF THE INVENTION

This invention relates to a method and materials that are designed for use in automating urinalysis. This system is designed to analyze urine for its constituents by a method that is fully automated (does not require the use of manual methods such as refractometer, pH meter, dipsticks, etc). Automation as designed by this system is directed to the use of a self-operating instrument that is capable of handling multiple reagents designed for use on an automated analyzer system for the quantitative determination of blood in urine.

It is known that the most common method for the analysis of urine is by the use of a manual technique known as a dipstick. This method for the analysis of urine is labor, time intensive, and costly among other detriments. The use of a dipstick for analysis of urine also relies on the subjective interpretation of the technician. The dipstick method requires the technician to submerge the dipstick in a sample of urine and remove it. To wait a specified time, then compare the color development of the test on the dipstick to a color chart. Even more cumbersome methods involve the use of a refractometer, pH meter, or manual chemistry test.

The following list of assay devices utilizing prior art includes dry tablets, dipsticks, or other manual techniques for the analysis urinary constituents. None of the prior devices foresee or teach of a multiple/single liquid reagent system designed specifically for auto-analyzers to analyze urinary constituents quantitatively.

One such U.S. Pat. No. 4,147,514 discloses test strips (dipsticks) for the detection of ketone bodies. The assay strips are made up of a chemical bonded to a cellulose pad on a strip. This is then dipped into a specimen sample. This method only determines ketone bodies qualitatively at its best, due to inability of the system to allow the use of standards and controls on the same strip the sample is applied to.

Another such patent, U.S. Pat. No. 3,146,070 discloses analytical compositions in dry form on a bibulous carrier (dipstick) impregnated with a pH indicator for the determination of pH. This assay at best only determines pH qualitatively, due to the inability to use standards and controls located on the same strip for the same test sample to define and verify a quantitative determination.

Additionally, U.S. Pat. No. 4,318,709 discloses a device comprising a carrier matrix (dipstick) impregnated with the test means for specific gravity. This assay at best only determines specific gravity qualitatively, due to the inability to use standards and controls located on the same strip for the same test specimen. The prior art in this case also did not foresee the wide specimen to specimen matrix variations of real world urine samples including matrix components such as pH, and ionic strength, and the concomitant requirement of a multiple reagent system to effectively analyze urine for specific gravity in a liquid to liquid reaction. The normal pH value for urine can range from 4.5 to 8.0, which if using the prior dipstick method the results would be vastly scattered and inaccurate without a reagent to neutralize the effect prior to completion of the assay.

Various devices are described in the literature for the determination of particular urinary constituents one by one with the use of carrier matrices (dipstick, microcapsules, filter pater, etc.). None of the prior art teaches or elucidates a means for determining by automated technology urinary constituents from a single sample of urine, via multiple tests that are reported simultaneously by an autoanalyzer using liquid reagents specifically designed for this family of instruments. As cited by the prior art, (in package insert literature) when evaluating laboratory test results, definitive diagnostic, or therapeutic decisions should not be based on any single result or method. However, the prior art states that dipsticks are affected by substances that cause abnormal urine color, such as drugs containing azo dyes (e.g., Pyridium, Azo Gantrisin, Axo, Gantanol), nitrofurantoin (Macrodantin, Furadantin), and riboflavin, and thus may affect the readability of reagent areas on the urinalysis reagent strips (dipsticks). The color development on the reagent pad may be masked, or a color reaction may be produced on the pad that could be interpreted visually and/or instrumentally as a false positive or negative.

SUMMARY OF THE INVENTION

The automated urinalysis system of this invention offers a method for reducing the consumable materials, and labor costs. The system also offers increased accuracy, sensitivity, and objective quantifiable determinations of urinary constituents for better diagnostic interpretation of the test results of urine, thus enabling a physician to provide better health care for the patient.

This invention satisfied many of the problems unanswered by the prior art: quantitative results, non-subjective results, reproducible results, increased accuracy, precision, sensitivity, carrier free reagents, reagents designed for autoanalyzer use, reagents uniquely designed for each particular urine analyte assay overcoming matrix problems previously unanswered by prior art, a method allowing vast improvement of test completion time (hundreds to thousands per hour). The present invention presents a fully automateable walk-away urinalysis system applicable to any discrete autoanalyzer currently in use, and obviously represents a marked advancement in the art of urinalysis. The clear cut object of the present invention is to provide a more comprehensive method for determining urinary constituents (Leukocytes, Blood, Bacterial Nitrite/Indole/reductase activity, Total Ketone bodies, Glucose, Protein, pH, and specific gravity) that in general benefit society as a whole and specifically yield improved health care.

Thus, it is a primary objective of the present invention to provide techniques for determination of urinary constituents (blood, Red Blood Cells/Hemoglobin), at low chemically significant levels.

An additional object of this invention is to make available an advanced method for analyzing a sample of urine for the quantitation of its constituents on an autoanalyzer. The advanced ability of the automated urinalysis system to offer a means for automated analysis on urine is a significant improvement in the art of urinalysis.

Additionally, the object of this invention is to provide a comprehensive method which is broadly adaptable to a wide variety of automated analyzers presently in use in the industry which will increase accuracy, sensitivity, precision, and speed. An autoanalyzer allows for precise quantitative results beyond the scope and abilities of the prior art. An autoanalyzer used in conjunction with the present invention automated urinalysis reagents provides a system that produces an objective quantitative result of an unknown urine sample obtained from a linear standard curve determined by analysis of standards run on the instrument, and verified as accurate by quantifying controls of known value. This simultaneous analysis of standards and unknowns (urine samples) yielding unbiased results improves the art of urinalysis significantly over the prior art, which yields only qualitative and subjective results.

It is a further object of this invention to provide a method for the simultaneous determination of multiple urinary components (Leukocytes, Blood, Bacterial Reductase/Nitrite/Indole activity, Total Ketone bodies, pH, Specific Gravity, Protein) from a single urine sample using a system of reagents designed for autoanalyzer use. This improvement in the science of urinalysis over the prior art proves to be significant medically and economically.

Another object of this invention is to provide a method that yields quantifiable results in the determination of urinary constituents present in a sample of urine.

Still another object of this invention is to provide a method for the determination of objective results (from the photometric analysis by the automated analyzer) instead of the subjective determination (from human observation). The present invention provides a unique formulated reagent system that can be mixed with unknown urine samples, standards, and controls and then be read spectrophotometrically with unbiased accuracy on an autoanalyzer. The use of the automated urinalysis system provides a means for improved accuracy, precision, and specificity by removal for the subjective human element from the analysis. Clearly, a system that automatically dispenses, measures, and records results is a marked improvement in the science of urinalysis.

Yet another object of this invention is to provide uniquely formulated reagents for each urinalysis assay that were not taught or envisioned by the prior art, and overcome the inadequacies of the prior art. The analysis for Blood in urine in the prior art is a carrier dependent assay that is susceptible to interference from urea, vitamin C, and high levels of some other normal urinary constituents. Consider the fact that urea is the largest component of urine (besides water) by a factor of 50% over the next largest component (sodium chloride). A unique chemical formulation to compensate for urea is an advancement in the art of urinalysis. The present invention is a liquid reagent that is not carrier dependent, designed for autoanalysis, and has agents added to remove the urea and other interfering ions from the solution, thus preventing it from interacting with the color developer. These improvements increase sensitivity, accuracy, and precision, thereby allowing the Blood assay in urine to be quantifiable.

DETAILED DESCRIPTION OF THE INVENTION

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process, represents a significant improvement over the present art. These improvements which facilitate application to automation and represent significant technical improvement over the previous art include, a buffering system for pH variation in urine by correcting pH to the analytically preferred value prior to analysis and also stabilizing reaction rates thereby improving linearity and neutralizing the interference effects of the highly complex matrix of random urines submitted for analysis. Additional technical improvement is due to the addition of components to remove interfering substances yielding reduced assay limitations and increased linearity, accuracy and precision in the resulting quantitations. These unique reagent formulations allow automation resulting in, but not limited to, enhanced speed, objectivity, accuracy and sensitivity associated with the automated test. A synopsis of the automated testing process follows. The entire automated urinalysis reagent system is loaded into an autoanalyzer. The controls, standards and unknown urine samples are fed into the autoanalyzer, individually mixed with each test reagent in discrete cuvettes, the absorbance read and quantitation determined for comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age and physical well being of the patient. All of the factors can interfere with the previous art.

The automated urinalysis system reagents are individually designed for optimum analysis of the specific urinary component. The reagent system to detect Blood (RBC's) in urine is carrier independent and contains specific agents added to compensate for interference by urea, vitamin C, high ionic levels (specific gravity), abnormal pH and other normal urinary constituents. The RBC reagent system is composed of two reagents (but can be consolidated into one). The first reagent (R1) is specifically designed to neutralize matrix interference and increase sample-reagent reagent compatibility, with the autoanalyzer. 2, 3-Butanedione monoxime is added to the first reagent (R1) to remove urea and other substances in the urine sample that cause interference with colorimetric reactions utilizing any of the following components: 3,3'5,5'-Tetramethylbenzidine, Dicarboxidine, 3-Methyl-2-benzothiazolinone hydrazone, or N, N-dimethylaniline. The components listed above are particularly susceptible to interference from urea (a major component of urine). Ethylenediaminetetraacetic acid (disodium salt), 0.15M succinic acid and dimercaptopropanol are other components of the R1 used to neutralize interfering substances by chelation and anti-oxidant activity. This compound removes oxidizing contaminants such hypochlorite and acts as a solution clarifier. It causes the disappearance of the characteristic yellow color of urine, thereby enhancing spectrophotometric analysis. 2,3-Diphosphoglycerate is added to affect the oxygen disassociation of hemoglobin. Saponin or 25% acetic acid is present to lyse the red blood cells that may be present and intact in urine, thus releasing the hemoglobin contained within. Note that 2,3-Diphosphoglycerate in the alkaline reagent mixture causes the disassociation constant of hemoglobin to shift to the left (acid Bohr effect), thus increasing the affinity of hemoglobin for oxygen and forcing the reaction to completion. Oxygen is provided by the reaction of hemoglobin with hydrogen peroxide. Sodium azide is added to stabilize hydrogen peroxide. The R2 contains a 30% solution of hydrogen peroxide acting as a substrate for the peroxidase activity of the heme fraction of hemoglobin which is a major component of red blood cells. The R1 also contains a buffer to adjust sample pH and aid in solubility and compatibility with R1's complex chemical matrix. This complex reagent matrix requires a complementary buffering system with unique dynamics, capable of adjusting the reaction solution to the ideal pKa and promoting component solution compatibility of the aqueous medium with autoanalyzers. Unbuffered solutions may have high acidic or basic activity, or strictly organic properties which are not compatible with autoanalyzer syringes, tubing, metal and plastic parts. This reagent system buffer is designed to correct these problems. The buffers also promote carrier independence. The R1 also contains surfactants that decrease surface tension, promote effective mixing on a molecular level and improve flow dynamics through tubing and syringes of automated analyzers. The concentrations of R1 buffers and components can be varied to compensate for limitations and variations in the configuration of sampling and reagent delivery systems of various makes of autoanalyzers. The R1 components compensate for abnormal urinary pH and highly buffered urines. Ampyrone is added to the R1 to promote, or catalyze the reaction of the aforementioned oxidized peroxide molecule with a coupling agent such as -hydroxybenzoic, N-Ethyl-N-sulfohydroxypropyl-m-toluidine (TOOS), 2-Hydroxy-3,5-dichlorobenzenesulfonate sodium sale (HDCBS), 2, 2'-Azino-di-3-ethylbenzthiazoline sulfonic acid diammonium salt (ABTS), or trinder, or phenolic substitutes. The addition of Pyrogallol is added to R1 and acts as a substrate that is oxidized by the oxygen radical released when the heme (peroxidase active) molecule reacts with hydrogen peroxide in solution.

The second reagent (R2) of the two part reagent system for Blood (if a single reagent system for Blood is not used) is composed of one, or more of the following: 3,3'5,5'-tetramethylbenzidine, dicarboxidine, pyrogallol, hydrogen peroxide, 3-methyl-2-benzothiazone hydrazone, N,N-dimethylaniline, benzidine, o-dianisidine and oxidized phenothiazines in solution. This reagent is buffered according to which group or single component is used. This buffer contained in R2 adjusts sample pH and aids in solubility and compatibility of R2's complex chemical matrix. This complex reagent matrix requires a complementary buffering system with unique dynamics capable of adjusting the reaction solution to the ideal pKa's, establishing carrier independence and promoting component solution compatibility in an aqueous medium with autoanalyzers. Unbuffered solutions may have high acidic or basic activity or strictly organic solubilities properties which are not compatible with autoanalyzer syringes, tubing, metal and plastic parts. The R2 also contains a color indicator such as 2,2'azinobis (3-ethylbenzothiazoline)-6-sulfonic acid and surfactants that decrease surface tension, promote effective mixing on a molecular level, enhance carrier independence and improve flow dynamics through tubing and syringes of automated analyzers. The combinations and concentrations of R1 and or the R2 components can be varied due to limitations and variations in the configuration of sampling and reagent delivery systems of different makes of autoanalyzers.

The preprogrammed monochromatically specified wavelength employed depends on the autoanalyzer employed, but will generally range from 340 to 700 nanometers.

Without further elaboration, it is believed that one skilled in the art can, using the preceding description, effectively utilize the present invention. The following preferred specific embodiments are, therefore, to be merely illustrative and not limitive of the remainder of the disclosure of the present invention in any way whatsoever. In the following examples, all instrument parameters, reagent combinations and method techniques are set forth.

EXAMPLE 1

The automated RBC urinalysis reagent system's first reagent (R1) contains surfactant, 2, 3-Butanedione monoxime, ethylenediaminetetraacetic acid, dimercaptopropanol, saponin, 2,3-Diphosphoglycerate and buffer. The second reagent (R2) consists of surfactant, buffer, 3,3',5,5'-tetramethylbenzidine in 10% lactic acid. These reagents are placed in the autoanalyzer. The urine samples, standards and controls are placed in the autoanalyzer specimen cups. The urine samples, standards and controls are aliquoted into cuvettes, mixed with the first reagent and then mixed with the second reagent and then read at specified intervals as dictated by the instrument parameters and at the specified wavelengths (monochromatically) depending on reagent combination used. In this instance, the assay should be read at 660 nanometers with read times specific to the analyzer.

EXAMPLE 2

The automated RBC urinalysis single reagent system would contain (all or some of the following:) 2,3-butanedione monoxime, ethylenediaminetetraacetic acid, dimercaptopropanol, 2,3-diphosphoglycerate, Ampyrone, sodium azide, hydrogen peroxide, saponin, p-hydroxybenzoic acid, N-ethyl-N-sulfohydroxypropyl-m-toluidine. The reagents are placed on the autoanalyzer. The urine samples, standards and controls are placed in the autoanalyzer specimen cups. The urine samples, standards and controls are aliquoted into cuvettes, mixed with the reagent and the solutions are read at specified intervals as dictated by the instrument parameters and the specified wavelength (monochromatically) depending on the reagent combination used. In this instance, the assay should be read at 505 nanometers read times are specific to the analyzer.

EXAMPLE 3

In the automated RBC urinalysis reagent system, first reagent (R1), contains surfactants, buffer, saponin, and etheylenediaminetetraacetic acid. The second reagent (R2) consists of hydrogen peroxide, 3-methyl-2-benzothiazoline hydrazone, N,N-dimethylanilane, buffers and surfactants. The reagents are placed on the autoanalyzer. The urine samples, standards and controls are placed in the autoanalyzer specimen cups. The urine samples, standards and controls are aliquoted into cuvettes with the first reagent. The second reagent is then added and mixed and the solutions are then read at specified intervals as dictated by the instrument parameters at the specified wavelength (monochromatically) depending on the reagent combination used. In this instance, the assay should be read at 585 nanometers and read times are specific to the analyzer.

EXAMPLE 4

In the automated RBC urinalysis reagent system's first reagent (R1) contains a buffer. The second reagent R2 consists of buffer, o-dianisidine. The reagents are placed on the autoanalyzer. The urine sample, standards and controls are placed in the autoanalyzer specimen cups. The urine samples, standards and controls are aliquoted into cuvettes, mixed with the first reagent, the second reagent is then added and mixed and the solutions are then read at specified intervals as dictated by the instrument parameters at the specified wavelength (monochromatically) depending on the reagent combination used. In this instance, the assay should be read at 540 nanometers and read times are specific to the analyzer.

EXAMPLE 5

In the automated RBC urinalysis the single reagent system would contain all or some of the following: 2,3- butanedione monoxime, pyrogallol, ethylenediaminetetraacetic acid, p-hydroxybenzoic acid, hydrogen peroxide, N-ethyl-N-(2-hydroxy-3-sulfopropyl)-m-toluidine and surfactants. The reagents are placed on the autoanalyzer. The urine samples, standards and controls are placed in the autoanalyzer specimen cups. The urine samples, standards and controls are aliquoted into cuvettes, mixed with the reagent, and the solutions are read at specified intervals as dictated by the instrument parameters at the specified wavelength (monochromatically) depending on reagent combination used. In this instance, the assay should be read at 550 and read time is specific to the analyzer.

EXAMPLE 6

The automated RBC urinalysis reagent system's first reagent (R1) contains ethylenediaminetetraacetic acid and buffer. The second reagent R2 consist of buffer and oxidized phenothiazines. The reagents are placed on the autoanalyzer. The urine samples, standards and controls are placed in the autoanalyzer specimen cups. The urine samples, standards and controls are aliquoted into cuvettes, mixed with the first reagent, then the second reagent is then added and mixed and the solutions are then read at specified intervals as dictated by the instrument parameters at the specified wavelength (monochromatically) depending on the reagent combination used. In this instance, the assay should be read at 540 nanometers and read times are specific to the analyzer.

EXAMPLE 7

In the automated RBC urinalysis reagent system's first reagent (R1) contains surfactant, 2,3-diphosphoglycerate, hydrogen peroxide, and buffer. The second reagent R2 consist of surfactant, buffer, p-hydroxybenzoic acid and phenol. The reagents are placed on the autoanalyzer. The urine samples, standards and controls are placed in the autoanalyzer specimen cups. The urine samples, standards and control are aliquoted into cuvettes and mixed with the first reagent. The second reagent is then added and mixed and the solutions are then read at specified intervals as dictated by the instrument parameters at the specified wavelength (monochromatically) depending on the reagent combination used. In this instance, the assay should be read at 505 nanometers and read times are specific to the analyzer.

EXAMPLE 8

The automated RBC urinalysis reagent system's first reagent (R1) contains ethylenediaminetetraacetic acid, 2,3-diphosphoglycerate, hydrogen peroxide, surfactants and buffers. The second reagent (R2) has buffers, surfactants, N-ethyl-N-sulfohydroxypropyl-m-toluidine. The reagents are placed on the autoanalyzer. The urine samples, standards and control are aliquoted into cuvettes, mixed with the first reagent, the second reagent is then added and mixed and the solutions are then read at specified intervals as dictated by the instrument parameters at the specified wavelength (monochromatically) depending on the reagent combination used. In this instance, the assay should be read at 550 nanometers and read times are specific to the analyzer.

EXAMPLE 9

The automated RBC urinalysis reagent system's first reagent (R1) contains hydrogen peroxide, surfactants and buffers. The second reagent (R2) consists of buffers, surfactants, N-Ethyl-N-sulfohydroxypropyl-m-toluidine (TOOS) and/or (one or more from the following group:

2,2'azino-di-(3-ethylbenzthiazoline) sulfonic diammonium salt (ABTS), 2-hydroxy-3,5-dichlorobenzenesulfonate sodium salt (HDCBS) or other suitable trinder reagent. The reagents are placed on the autoanalyzer. The urine samples, standards and control are aliquoted into cuvettes and mixed with the first reagent. The second reagent is then added and mixed and the solutions are then read at specified intervals as dictated by the instrument parameters at the specified wavelength (monochromatically) depending on the reagent combination used. In this instance, the assay should be read at 550 nanometers and read times are specific to the analyzer.

EXAMPLE 10

A liquid reagent is successfully compounded by dissolving the following chemicals at room temperature (25 degree C.):
Solution I
0.001M Succinate buffer
0.1 g ABTS, 2,2'-Azinobis(3-ethylbenzthiazolinesulfonic acid)
250.0 ml glacial acetic acid
Distilled water to 1000 ml total volume of solution
Solution II
1000 ml
30.0 g hydrogen peroxide, urea adduct total volume of solution A sample of Hemoglobin containing urine is obtained which, upon mixing with the liquid reagents, gives a measurable response after about 5 to 20 seconds. The sensitivity is about 0.001 mg/dl to 1.0 g/dl hemoglobin, under certain circumstances intact cells (RBC's) can still bring about a measurable response with the liquid chemistry test.

Note that glacial acetic acid in the Example 10 plays a multiple role of buffering the reagent solution, lysing red blood cells, and neutralizing some types of urinary interferomes. The ABTS acts as a color indicator in this example. Other indicators that will function in this example in place of ABTS include:
2,2'-Azino-bis(3-ethylbenzthiazoline-6-Sulfonic Acid
o-Phenylenediamine
3,3',5,5'-Tetramethylbenzidine
o-Dianisidine
5-Aminosalicylic Acid
3,3'-Diaminobenzidine
3-Amino-9-Ethylcarbazole
4-Chloro-1-Napthol
o-Tolidine
Dicarboxidine
phenothiazines
p-Hydroxybenzoic Acid Other compounds that are attenuating agents and can be substituted for the 6-methoxyquinoline in like amount by weight are:
1. Benzoquinolines
   1.1 benzo [c] quinoline (phenanthridine)
   2-methylphenanthridine
   6-methylphenanthridine
   2-ethylphenanthridine
2. Dibenzoqninolines
   2.1 dibenzo [c,f] quinoline (benzo [g] phenanihildine)
3. Pyridoqulnolines
   3.1 pyrido [2, 3-f] quinoline (1, 7-phenonthroline)
   2-methyl-a, 7-phenanthroline
   3.2 pyrido [3, 2-f] quinoline (4, 7-phenanthroline)

3-methyl-4, 7-phenanthroline
3, 8-dimethyl-4, 7-phenanthroline
3,3 pyrido [2, 3-f] quinoline (1, 6-anthrazoline)
2, 7-dimethyl-1, 6-anthrazoline
2-methyl- or 2-ethyl-phenanthrldine
benzo [f] quinoline
1, 2-tetramethylenobenzo [f] quinoline
dibenzo [c, f] quinoline
pyrido [3,2-f] quinoline
3-methyl-4, 7-phenanthroline
pyrido [2, 3-f] quinoline
3-methylbenzo [f] quinoline
1, 3-dimethylbenzo [f] quinoline
2, 4-dimethylbenzo [g] quinoline
3, 2-dimethyl-4, 7-phenanthroline

EXAMPLE 11

A typical automated analyzer for use in the detection system of this invention is a HITACHI 717. The performance data for a red blood cell test is as follows:

| CHEMISTRY PARAMETERS | |
| --- | --- |
| TEST | [RBC] |
| ASSAY CODE | [2 POINT] : [26] - [36] |
| SAMPLE VOLUME | [10] |
| R1 VOLUME | [250] [100] [NO] |
| R2 VOLUME | [ 50] [100] [NO] |
| WAVE LENGTH | [700] [415] |
| CALIB. METHOD | [LINEAR] [0] [0] |
| STD. (1) CONC. -POS. | [ 0] - [ 1] |
| STD. (2) CONC. -POS. | [ 70] - [ 2] |
| STD. (3) CONC. -POS. | [ 0] - [ 0] |
| STD. (4) CONC. -POS. | [ 0] - [ 0] |
| STD. (5) CONC. -POS. | [ 0] - [ 0] |
| STD. (6) CONC. -POS. | [ 0] - [ 0] |
| SD LIMIT | [ 999] |
| DUPLICATE LIMIT | [32000] |
| SENSITIVITY LIMIT | [ 0] |
| ABS. LIMIT (INC/DEC) | [32000] [INCREASE] |
| PROZONE LIMIT | [ 250] [UPPER] |
| EXPECTED VALUE | [ –999] - [ 70] |
| TECH. LIMIT | [ –999] - [ 70] |
| INSTRUMENT FACTOR | [ 1.0] |

| PERFORMANCE CHARACTERISTICS | |
| --- | --- |
| Precision: Precision studies were conducted using human urine control on the Hitachi 717 over a period of 30 days and yielded the following results: Red Blood Cell | |
| Within Run | Day to Day |
| n = 20 | n = 20 |
| mean = 29.70 | mean - 29.64 |
| SD = 0.47 | SD = 1.67 |
| CV (%) = 1.58 | CV (%) = 5.62 |

ACCURACY (METHOD COMPARISON):

A comparison of this method on the Boehringer Mannheim/Hitachi 717 Analyzer using the Ames dipstick as the reference resulted in the following linear regression
Statistics: Red Blood Cells
y = a * x + b a = 0.8132305, b = 0.7752521, Correlation = 0.91650, n = 25

We claim:

1. A method for quantitatively detecting red blood cells in a patient's urine employing an automated analyzer the steps comprising placing an aliquot of the urine to be tested in an automated analyzer sampling cup, placing the cup in a sampling tray within the automated analyzer, transferring the urine to a cuvette mounted within the automated analyzer, injecting at least one reagent composition in an aqueous medium into the cuvette, the reagent composition containing a buffer to adjust the pH of the urine to a preferred value, a compound to lyse the red blood cells in the urine, a substrate to react with the red blood cells and a color indicator to quantitatively determine blood cells in the urine wherein said indicator is 2.2'-Azino-bis(3-ethylbenzthiazoline-6-Sulfonic Acid), reading at specified intervals, in accordance with a pre-programmed code introduced into the automated analyzer, at a preprogrammed monochromatically specified wavelength, to compare absorbance of the patient's urine and reagent composition complex with that of a standard containing a known concentration of hemoglobin and thereby determining the presence or absence of blood cells in the patient's urine.

2. The method according to claim 1 wherein in the at least one reagent composition there is a first and second composition injected into the cuvette, the first composition containing at least one compound to neutralize urine pH interference and lyse red blood cells and the color indicator and the second reagent composition containing the substrate.

3. The method according to claim 1 wherein the color indicator in the reagent composition is 2,2'-Azino-bis(3-ethylbenzthiazoline-6-sulfonic acid.

4. The method according to claim 1 wherein the wavelength of the analyzer is about 340 to 700 nanometers.

5. The method according to claim 2 wherein the at least one compound to neutralize urine pH interference and lyse red blood cells is glacial acetic acid.

6. The method according to claim 2 wherein the second reagent substrate is hydrogen peroxide.

* * * * *

UNITED STATES PATENT AND TRADEMARK OFFICE
CERTIFICATE OF CORRECTION

PATENT NO. : 5,733,785
DATED : March 31, 1998
INVENTOR(S) : Jack V. Smith, et al.

Page 1 of 1

It is certified that error appears in the above-identified patent and that said Letters Patent is hereby corrected as shown below:

<u>Title page,</u>
Item [73] Assignee, Delete "Chinera Research Chemical, Inc." and insert -- Chimera Research & Chemical, Inc. --.

Signed and Sealed this

Twenty-fifth Day of September, 2001

Attest:

Attesting Officer

NICHOLAS P. GODICI
*Acting Director of the United States Patent and Trademark Office*